United States Patent
Lee et al.

(10) Patent No.: US 6,376,658 B1
(45) Date of Patent: Apr. 23, 2002

(54) PROTEINS RELATED TO ENCAPSULATION AND GENES ENCODING THE SAME

(75) Inventors: Bok Luel Lee; Mi Young Cho, both of Pusan; Chong Jin Park; Seung-Suh Hong, both of Taejon; Hyun-Soo Lee, Seoul, all of (KR)

(73) Assignee: Samyang Genex Corporation, Seoul (KR)

( * ) Notice: Subject to any disclaimer, the term of this patent is extended or adjusted under 35 U.S.C. 154(b) by 0 days.

(21) Appl. No.: 09/521,780

(22) Filed: Mar. 9, 2000

(30) Foreign Application Priority Data

Jul. 7, 1999 (KR) .......................................... 1999-27933
Jul. 26, 1999 (KR) .......................................... 1999-31172

(51) Int. Cl.[7] .......................... C07H 21/04; C07K 1/00; C07K 16/00; A61K 39/00
(52) U.S. Cl. ...................... 536/23.1; 536/23.7; 530/350; 530/388.4; 530/389.5; 424/185.1; 424/265.1
(58) Field of Search .............................. 530/350, 388.4, 530/389.5; 536/23.1, 23.7; 424/185.1, 265.1

(56) References Cited

PUBLICATIONS

1. Mi Young Cho, et al., "Molecular Cloning and Functional Properties of Two Early–Stage Encapsulation–Relating Proteins From The Coleopteran Insect, Tenebrio Molitor Larvae", The FEBS Journal (Euro. J.. Biochem.), vol. 262, No. 3, Jun. 11, 1999.

2. Mi Young Cho, et al., "An 86 kDa Diapause Portein 1–Like Protein Is A Component of Early–Staged Encapsulation–Relating Proteins In Coleopteran Insect, Tenebrio Molitor Larvae", FEBS Letters, vol. 451, (1999) 303–307.

*Primary Examiner*—Hankyel T. Park
(74) *Attorney, Agent, or Firm*—Darby & Darby

(57) ABSTRACT

The present invention relates to a protein related to encapsulation in immune reaction and a gene encoding the same.

13 Claims, 2 Drawing Sheets

PROTEINS RELATED TO ENCAPSULATION AND GENES ENCODING THE SAME

TECHNICAL FIELD AND BACKGROUND ART

The present invention relates to proteins related to encapsulation.

The present invention also relates to genes encoding proteins related to encapsulation.

All living organisms have immune systems to protect themselves from foreign materials such as invading pathogens. The immune reactions are categorized into inherent immune reaction and acquired immune reaction. The main differences between these two immune reactions lie in how the foreign material that invades into a body is recognized. Acquired immune reaction is a differentiated and complex immune system where B or T lymphocytes recognize specific portions of a foreign material and produce immunoglobulins. On the other hand, inherent immune reaction is a somewhat non-specific and less-differentiated immune system where components that exist commonly on microbial cell walls are recognized. Acquired immune reaction, however, is known to lack an ability to distinguish the pathogens from self-antigen for which an immune reaction is not required. Recent reports indicate that inherent immune reaction performs a leading role in the antigen selection of B or T lymphocytes in acquired immune reaction.

As the similarities are found between the immune system of mammals and insects, such as Drosophila which has an inherent immune system only, insect immune reaction is considered as a good model system to study the inherent immune system. An insect's immune system can be categorized mainly into humoral and cellular immune reactions. There are examples of cellular immune reaction wherein small foreign materials such as bacteria or fungi are eliminated by phagocytosis and when very large foreign materials such as mycelia or parasites invades, they are surrounded completely by many blood cells through an encapsulation reaction. Encapsulation reaction has only been studied by microscopic observations to date. However, few studies were performed on a molecular level.

It is known that malaria larva or eggs of vespidae can survive in their host only under a condition that the malaria larva or the eggs of vespidae secrete materials which inhibit encapsulation reaction. It is unknown, however, what inhibits or induces encapsulation. Pneumoconiosis in mammals is a similar reaction to encapsulation, but the mechanism or the related materials are not known.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE INVENTION

Figure 1A:
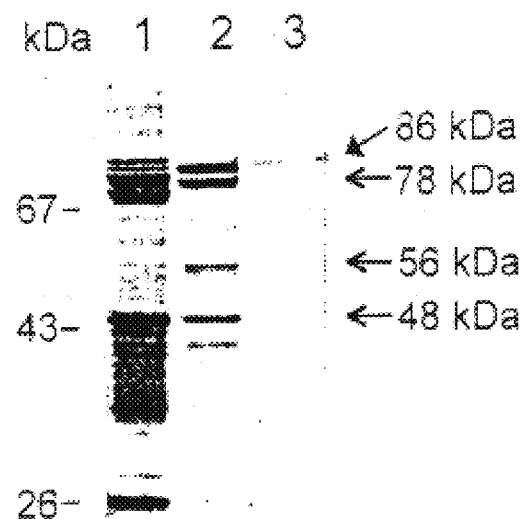
FIGS. 1A and 1B are electrophoresis photographs showing the presence of encapsulation protein according to the present invention.

The present invention relates to novel proteins related to encapsulation. Proteins of the present invention can be used as therapeutics for malaria or pneumoconiosis.

Terminology and techniques in the present application have the meanings that are generally used in the field that the present invention belongs unless otherwise specified. Also the references mentioned in the present application are the references to explain the present invention and are incorporated by reference in the present application.

"Amino acid sequence", "polypeptide" and "protein" are not limited to the perfectly natural amino acid sequence.

"Base sequence variants" refer to altered base sequence due to substitution, deletion or addition of one or more bases in gene sequence of the present invention while maintaining biological or immunological activity.

"Amino acid sequence variants" refer to an altered amino acid sequence due to substitution, deletion or addition of one or more amino acids in the amino acid sequence of the present invention while maintaining biological or immunological activity.

"Encapsulation protein derivatives" refer to a protein wherein one or more base sequences of a gene encoding encapsulation protein are altered while maintaining the biological characteristic of the protein that it encodes.

The present invention relates to a gene represented by Sequence 1 or Sequence 4, its fragments, its variants, its derivatives and their alleric variants.

The gene encoding encapsulation protein according to the present invention was isolated from larva of coleopteran *Tenebrio molitor*.

The present invention also relates to an encapsulation protein represented by Sequence 3 or Sequence 6, its fragments, its variants and its derivatives.

The compositions of the buffer solutions used in the present invention are as follows.

Entomological physiological saline (pH 6.0): NaCl 130 mM, KCl 5 mM, $CaCl_2$ 1 mM Anticoagulation buffer (pH 4.6): trisodium citrate 136 mM, citric acid 26 mM, NaCl 15 mM, EDTA 20 mM Elution buffer (pH 6.5): Urea 6 M, SDS 0.2%, DTT 5 mM, Tris 50 mM Skim milk solution used in antibody purification (pH 7.9): skim milk 2.5 g dissolved in 20 mM Tris/HCl 50 ml (pH 7.9)

10×washing buffer used in antibody purification: Tris 100 mM, EDTA 10 mM, Triton X-100 1%, NaCl 1.5 M Washing buffer used in antibody purification: 1× washing buffer containing skim milk 0.5%, $NaN_3$ 2 mM TBS: Tris 20 mM, NaCl 153 mM TTBS: Tris 20 mM, NaCl 153 mM, Tween 20 0.1%

Filter to be treated IPTG: IPTG 190.6 mg, distilled deionized water (DDW) 40 ml

High-TBST solution: 1 M Tris-HCl (pH7.9) 30 ml, NaCl 5.25 g, 20% Tween 20 15 ml, quantity sufficient with distilled and deionized water (DDW) to 600 ml solution.

Low-TBST solution: 1 M Tris-HCl (pH 7.9) 20 ml, NaCl 17.5 g, 20% Tween 20 5 ml, quantity sufficient with distilled and deionized water (DDW) to 2 L solution.

3% gelatin solution: gelatin 12 g, 10% $NaN_3$ 800 µl, quantity sufficient with low-TBST to 400 ml solution.

Primary antiserum solution: purified antibody 1.8 ml, 3% gelatin solution 1.8 ml, *E. coli* extract (1 mg/ml) 54 µl, 10% $NaN_3$ 54 µl, distilled and deionized water (DDW) 1.7 ml Secondary antiserum solution: 3% gelatin solution 1.7 ml in 5 ml of goat anti-rabbit IgG(H=L)-AP conjugated (Bio-Rad Co.) 5 µl AP buffer: 1 M Tris-HCl(pH 9.5) 30 ml, NaCl 1.74 g, 1M MgSO$_4$ 1.5 ml, quantity sufficient with distilled and deionized water (DDW) to 300 ml solution.

Colorization agent: AP buffer 100 ml, 50 mg/ml NBT 1320 μl in 70% DMF, 50 mg/ml BCIP 660 μl in DMF LB liquid medium: NaCl 10 g, trypton 10 g, yeast extract 5 g, quantity sufficient with distilled and deionized water (DDW) to 1 L medium.

NZY plate: NaCl 5 g, MgSO$_4$.7H$_2$O 2 g, yeast extract 5 g, NZ amine 10 g, bacto agar 15 g, distilled and deionized water (DDW) 1 L NZY plate (top agar): NaCl 5 g, MgSO$_4$.7H$_2$O 2 g, yeast extract 5 g, NZ amine 10 g, bacto agar 7 g, distilled and deionized water (DDW) 1 L SM buffer: NaCl 5.8 g, MgSO$_4$.7H$_2$O 2 g, 1 M Tris-HCl (pH 7.5) 50 ml, 2% gelatin 5 ml, quantity sufficient with distilled and deionized water (DDW) to 1 L solution.

The present invention will be further illustrated by the following examples. It will be apparent to those who have conventional knowledge in the field that these examples are given only to explain the present invention more clearly, and are not limited to the examples given.

EXAMPLE 1

Separation of Proteins Related to Encapsulation

Figure 1B:
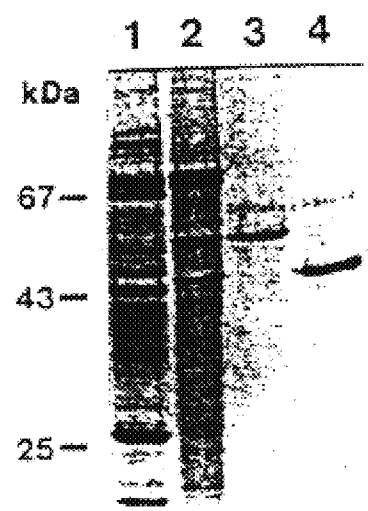

Twenty microliters of solution prepared by mixing 1 ml of entomological physiological saline with 1 g of DEAE-Sepharose CL-6B resin were injected into a larva of *Tenebrio molitor*, and the injection site was sealed immediately with a liquid paraffin. After 10 minutes, 50 μl of anticoagulation buffer was injected and body fluid was sampled by cutting the tail of the larva. After recovering the resin by centrifuging the body fluid, the resin was washed twice with anticoagulation buffer. The materials coated on the resin were obtained by washing them with 20 μl of 50 mM Tris-HCl(pH 7.0) containing 6M guanidine-HCl and 1 mM EDTA, and diluted with 1 ml of distilled deionized water. The proteins in the solution was precipitated by adding 100% TCA at 10% volume ratio to the total sample volume and reacted for 30 minutes at 4° C. After removing the supernatants by centrifuging the mixture at 4° C. at 15,000 rpm, the pellet was washed with cold acetone. The supernatant was removed again by centrifugation under identical conditions. After drying the precipitate, it was reduced by adding 2% 2-mercaptoethanol and thermally treated at 75° C. for 20 minutes and electrophoresised in 12% SDS-PAGE. The result is shown in FIG. 1. Four proteins of 86 kDa, 78 kDa, 56 kDa and 48 kDa were observed. Lane 1 in FIG. 1A is insect serum, lane 2 is protein extracted from those coated on the resin, and lane 3 is purified 86 kDa protein. Lane 1 in FIG. 1B is insect serum, lane 2 is protein extracted from those coated on the resin, lane 3 is purified 56 kDa protein, and lane 4 is purified 48 kDa protein After separating the bands of 48 kDa, 56 kDa and 86 kDa proteins related to encapsulation from SDS-PAGE gel, a single protein was obtained by electroelution.

In order to determine the partial amino acid sequence of the isolated pure protein, 30 μg of 0.4 M NH$_4$HCO$_3$ buffer containing 8 M urea was added to 30 μg of solution containing isolated protein. And 10% of 45 mM DTT based on the total sample volume was added to the same and then reacted for 15 minutes at 50° C. to reduce the sample. The reduced cysteine residues were alkylated by the addition of 100 mM iodoacetamide solution equivalent to 10% volume to the total sample volume and reacted for 15 minutes at room temperature. The product was precipitated by 10% TCA precipitation, and obtained proteins were dissolved in 0.4 M NH$_4$HCO$_3$ buffer containing 8M urea. Each proteins were fragmented by the reaction of 2 μg trypsin for 13 hours at 37° C. The fragmented proteins were separated with C18 reverse phase HPLC column (chemcosorb 5-ODS-H 2.1× 150/W 11660) by applying linear gradient [A; 0% CH$_3$CN in 0.06% TFA, B; 80% CH$_3$CN in 0.052% TFA] with increasing B solvent to 90% for 90 minutes at a flow rate of 0.2 ml per minute. The amino acid sequence was determined by using Edman degradation.

To determine the N-terminal of the isolated and purified protein, electrophoresis was performed for 18 hours at a static current of 75 mA in transfer buffer (an aqueous solution containing 10 mM CAPS, 10% methanol (pH 11)) after performing 12% SDS-PAGE. The protein was transferred onto polyvinylidene difluoride (PVDF) membrane. After the membrane was dyed with Coomassie brilliant blue (CBB) colorizing solution (0.1% CBB R-250, 50% methanol), it was decolorized with decolorizing buffer (50% methanol, 10% acetic acid) and washed a few times with water and dried under reduced. pressures. The protein was isolated from membrane by cutting the band and then amino acid sequence was determined by using automatic amino acid sequencer.

N-terminal amino acid sequence of 56 kDa protein

S T V Y R N R N I S

Partial amino acid sequence of 56 kDa protein

I Q I N D N A L Y T P G

E Y Q G V V D E A Q Y K

G V Q T I G Q L R

N-terminal amino acid sequence of 48 kDa protein

G S L K G R T Q G D

Partial amino acid sequence of 48 kDa protein

Q Y Y P T S L N V N P L L G

L I G S Q Q V P Y V Q G

T I Q Q L L G I P Q

N-terminal amino acid sequence of 86 kDa protein

V S V Q N E P V T N P Q R

Partial amino acid sequence of 86 kDa protein

G E L F Y Y M Y

D P A F Y Q L F K

T S Y Y E V Y Q K

Instead of using 1 g of DEAE-sepharose CL-6B resin, 1 g of CM- sepharose CL-6B, 1 g of Bio-gel or 1 cm of suture each was injected to larva of *Tenebrio molitor* to induce the production of encapsulation protein.

EXAMPLE 2

Antibody Preparation of the Proteins Related to Encapsulation

Antibody preparation of 86 kDa protein

To prepare polyclonal antibodies of the protein related to encapsulation reaction, 1 ml of blood of a rabbit (white, male 2.7 kg) was drawn from an ear vein before forming antibodies and was incubated for 1 hour at 37° C. to induce blood coagulation. Serum portion was obtained by centrifugation and stored at −80° C. Twenty micrograms of 86 kDa protein obtained from Example 1 was suspended in an equal amount of Freund's complete adjuvant and injected at two different sites on the back of rabbits subcutaneously. The rabbits were repeatedly injected at 3 times a week interval with an equal amount of protein suspended in an equal amount of Freund's incomplete adjuvant subcutaneously. Three days after the last inoculation, the blood was collected from ear vein and heart and incubated for 1 hour at 37° C. to induce blood coagulation. Serum portion was obtained by centrifugation and stored at −80° C.

To purify the antibody, the proteins related to encapsulation were electrophoresed in 10% SDS-PAGE, transferred to PVDF membrane, and the protein bands were cut to be washed with washing buffer after reacting it with skim milk solution for 1 hour. The proteins were reacted overnight with twice-diluted antiserum obtained from the rabbit as above. After washing it with washing buffer, the protein was eluted with 0.2 M Glycine/HCl (pH 2.8) and neutralized immediately with 1 M KOH to pH 7.4 to obtain antibody of a 86 kDa protein related to encapsulation. Obtained antibody was aliquoted to be stored at −80° C.

Figure 2:
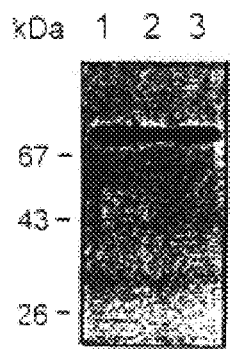
FIG. 2 is a photograph showing the result of immunoblotting using 86 kDa protein antibody.

After electrophoresing the proteins related to encapsulation obtained from Example 1 under reducing conditions by using 10% SDS-PAGE, they were transferred to PVDF membrane by reacting for 4 hours at 4° C. at 280 mA in transfer buffer. The membrane was washed with TBS, and cultured in a shaking incubator overnight at 4° C. in TBS supplemented with 5% skim milk and 1% horse serum to prevent non-specific reactions. Isolated antiserum diluted 100 times in TBS containing 2.5% skim milk was cultured in a shaking incubator for 2 hours at room temperature. Antiserum was washed 5 times with TTBS and reacted for 30 minutes at room temperature with a solution containing secondary antibody (anti-rabbit lg, total donkey antibody linked with western horseradish peroxidase) diluted 100 times in TTBS. The product was washed again 5 times with TTBS. By performing ECL blot for 1 minute under semi-dark condition, the produced fluorescence was sensitized to a film. The result is shown in FIG. 2. This antibody recognized 86 kDa protein specifically. Lane 1 in FIG. 2 is the purified 86 kDa protein, lane 2 is insect serum, and lane 3 is protein extracted from those coated on the resin.

Antibody preparation of 56 kDa protein and 48 kDa protein

By using the same antibody preparation procedure and separation method as the 86 kDa protein antibody, antibodies of the 56 kDa protein and 48 kDa protein were prepared.

After obtaining proteins related to encapsulation by injecting DEAE-sepharose CL-6B resin, CM- sepharose CL-6B, Bio-gel or suture respectively, these proteins were electrophoresed in 10% SDS-PAGE under reducing conditions, and transferred to PVDF membranes by reacting for 4 hours at 4° C. at 280 mA in a transfer buffer.

Figure 3:
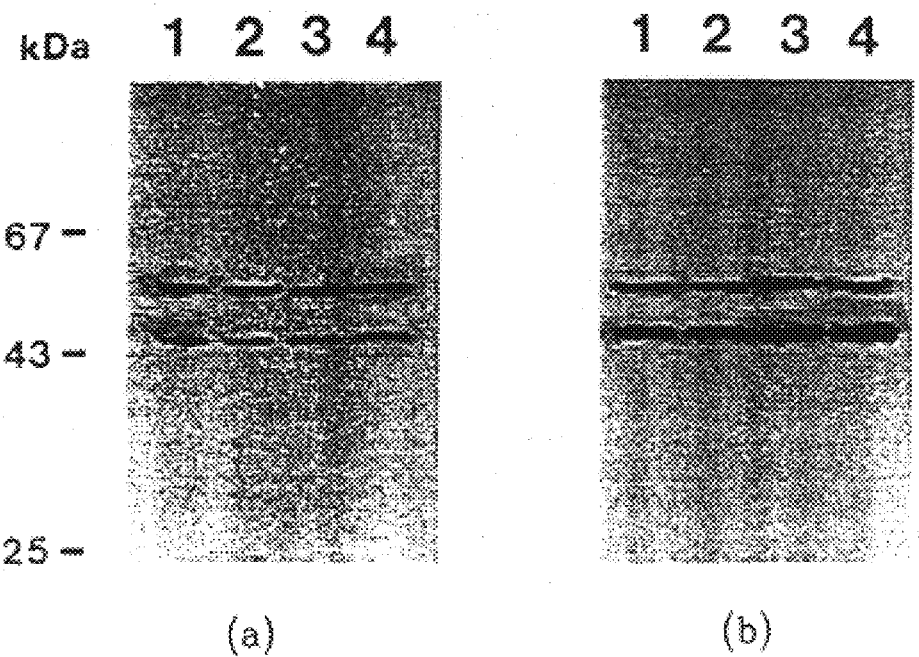
FIGS. 3A and 3B are photograph showing the results of immunoblotting using 56 kDa protein antibody and 48 kDa protein antibody, respectively.

The membrane was washed with TBS, and cultured in a shaking incubator overnight at 4° C. in TBS containing 5% skim milk and 1% horse serum to prevent non-specific reactions. Isolated antiserum diluted 100 times in TBS containing 2.5% skim milk was cultured in a shaking incubator for 2 hours at room temperature. Antiserum was washed 5 times with TTBS and reacted for 30 minutes at room temperature with a solution containing secondary antibody (anti-rabbit lg, total donkey antibody linked with western horseradish peroxidase) diluted 100 times in TTBS. The product was washed again 5 times with TTBS. By performing ECL blot for 1 minute under semi-dark condition, the produced fluorescence was sensitized to a film. The result is shown in FIG. 3A. Instead of antiserum for the 56 kDa protein, an experiment was performed by using the same procedure with antiserum for the 48 kDa protein. The result is shown in FIG. 3B. The antibodies for the 56 kDa protein and 48 kDa protein recognized specifically the 56 kDa protein and 48 kDa protein, respectively. Lane 1 in FIGS. 3A and 3B is the protein obtained by injecting Bio-gel, lane 2 is by injecting CM-sepharose CL-6B, and lane 3 is by injecting DEAD-sepharose CL-6B resin, and lane 4 is by injecting suture.

EXAMPLE 3

Separation of cDNA Encoding 86 kDa Protein

By immunoscreening, cDNA encoding the 86 kDa protein identified in Example 1 was separated.

XL-1-Blue was cultured by shaking incubation at 37° C. in 5 ml LB medium containing 20% maltose 50 $\mu$l, 1M Mg SO$_4$ 50 ml and it was harvested and suspended with 10 mM MgSO$_4$ to have an OD$_{600}$value of 0.5.

According to a method in the literature (Moon et. al. (1994) J. Biochem. (Tokyo) 116, 53–58), cDNA library of larva of *Tenebrio molitor* was made. 200 $\mu$l of XL-1-Blue was added to the cDNA library slution and cultured in a shaking incubator for 15 minutes at 37° C. The product was mixed with 3.5 ml of top agar preheated to 48° C., and the mixture was poured into a NZY plate. After 4 hours culture at 42° C., a filter treated with IPTG was carefully placed on the plate, and cultured further for 8 hours at 37° C. After the termination of the reaction, the plate was incubated for 20 minutes at 4° C., and the filter was dried completely in air. The dried filter was washed for 10 minutes at room temperature with high-TBST buffer, and further washed twice with low-TBST solution for 10 minutes at room temperature. The washed filter was dried completely and placed in 3% gelatin solution for blocking at 27° C. for 30 minutes. After drying the filter, it was reacted with antibody solution related to encapsulation for 2.5 hours at 27° C. After reaction, the filter was washed three times with low-TBST buffer and reacted in a secondary antibody solution for 30 minutes at 37° C. The filter was washed three times with low-TBST solution and underwent a colorization reaction.

The filter prepared as above was colorized by placing in a colorizing agent consisting of 100 ml of AP buffer supplemented with 1320 $\mu$l of 50 mg/ml NBT (nitroblue tetrazolium chloride, Bio-rad 170-6532) and 660 $\mu$of 50 mg/ml BCIP(5-bromo-4-chloro-3-indoylphosphate -p-toluidine salt Bio-rad 170-6539). The filter was completely dried in air. The purple clones distinguished clearly from surroundings were identified as primary positive clones. Primarily selected positive clones were diluted with SM buffer and, 200 $\mu$l of XL-1-Blue (OD$_{600}$=0.5) was added to an amount expected to produce 100–200 plaques and cultured in a shaking incubator for 15 minutes at 37° C. To this 3 ml of preheated top agar was added and poured in a NZY plate. Further procedure to select secondary positive clones was identical to that for primary selection.

To a 50 ml Falcon tube, 200 $\mu$l of XL-1-Blue (OD$_{600}$= 1.0), 200 $\mu$l of positive plaque solution identified through secondary selection (2×10$^5$ phage) and 1 $\mu$l of ExAssist helper phage were added and cultured in a shaking incubator for 15 minutes at 37° C., then 3 ml of LB liquid medium was added and cultured in a shaking incubator for 3 hours at 37° C. and thermally treated for 20 minutes at 70° C. The thermally treated solution was centrifuged for 15 minutes at 1000×g, and the supernatant was stored at 4° C. in a 15 ml Falcon tube.

To 200 $\mu$l of SOLAR cells (OD$_{600}$=1.0), 2 $\mu$l and 10 $\mu$l of phagemid diluted 10 times with LB liquid medium were added and cultured in a shaking incubator for 15 minutes at 37° C., and 50 $\mu$l each was smeared on a LB/ampicillin plate. Since XL-1-Blue pBlue-script has an ampicillin resistant gene and the host SOLR cell does not have ampicillin resistance, only transformed SOLR cells with phagemid can grow in a medium containing ampicillin. After culturing for 12 hours at 37° C., single colonies which were grown on LB/amphicillin plate were cultured for 12 hours at 37° C. in 5 ml of LB medium containing 10 μl of ampicillin (50 mg/ml). A DNA purification kit (Promega, wizard plus sv minipreps) was used to isolate and to purify a plasmid inserted with 86 kDa encoding from culture broth.

The gene encoding 86 kDa protein was analyzed by using commercially available DNA sequencing kit (Perkin Elmer, Rhodamine terminator cycle sequencing ready reaction). The base sequence was analyzed independently from 3'-and 5' ends by using the primers denoted as below, and two analysis results were compared to confirm the sequence (Sequence number 1). The protein sequence was deduced from the base sequence (Sequence numbers 2 and 3). The obtained gene has an open reading frame of 2262 nucleotides corresponding to 754 amino acids. It has been confirmed that there exist N-terminal amino acid sequence and 3 portions of amino acid sequences determined in Example 1.

Complimentary primer sequence for 5'-terminal
338 CTACGCCAACAACTGGGAA 357
56 CTGAAGACATCGGTGTCAAC 675
031 ATGTCATCGATCTGGGCTAC 1050
1481 ACTTCAAGGTGCAAGTTGCC 1500
1920 CCGCAAGACTGACATACCC 1938
Complimentary primer sequence for 3'-terminal
1872 TACGCCACCGTAAGATCCC 1854
1459 GAGTGACGTAGACAGCGTT 1441
1101 GAGACCTTCACTGCTGAAC 1083
720 GCTCATCCAGAAGGGATAG 702
366 GTAGAAGGTTTCCCA 380

It was confirmed that this gene is different from any known gene by performing homology search using protein sequence database of the National Center for Biotechnology Information (NCBI).

EXAMPLE 4

Isolation of cDNA Encoding 56 kDa Protein

According to the method of Chirgwin and others (Chirgwin, et. al., (1979) Biochemistry 18, 5294–5299), total RNA was isolated form larva of *Tenebrio molitor* and poly(A)-rich RNA was separated by using (dT)$_{30}$ latex bead therefrom. cDNA library of the above. poly(A)-rich RNA was constructed by using an expression vector Zap (Stratagene). According to the method of Short and co-workers (Short et. al., (1988) Nucleic Acids Res. 16, 7583–7600), cDNA library was constructed by using pBluescript.

To isolate cDNA encoding 56 kDa protein, the following nucleotide sequences were used as probes corresponding to partial amino sequences YQGVVDEA and QIQINDND, which are portions of the 56 kDa proteins.

5'-TA(T/C)CA(A/G)GGIGTIGTIGA(T/C)GA(A/G)GC 3'

5'-CA(A/G)ATICA(A/G)ATIAA(T/C)GA(T/C)AA(T/C)GC3'

The 5' ends of these DNA probes were tagged with [γ-$^{32}$P] ATP by using polynucleotide kinase.

To screen cDNA encoding the 56 kDa protein, membrane attached with Tenebrio phage cDNA was pre-hybridized for 5 hours in 3×SSC buffer [0.015M sodium citrate (1×Denhardt solution: 0.02 w/v Ficoll 400, 0.02 w/v bovine serum albumin, 0.02 w/v polyvinylpyrollidone 40, sonicated salmon sperm DNA 50 μg/ml) in 1×SSC buffer: 0.15M NaCl, Denhardt solution]. After this, the above two DNA probes were mixed with 1×Denhardt solution containing sonicated salmon sperm DNA 25 μg/ml and added to the membrane and hybridized for 12 hours at 45° C. The membrane was washed twice for 5 minutes at 45° C. in the presence of 4×SSC buffer. After the DNA of the obtained positive phage was extracted, it was inserted into the pBluescript plasmid, and the plasmid was extracted by using a plasmid preparation kit by Stratagene (note: J. Biochem. 116, 53–58 (1994)).

Gene encoding the 56 kDa protein was sequenced by using commercially available DNA sequencing kit (Perkin Elmer, Rhodamine terminator cycle sequencing ready reaction). The base sequence was analyzed independently from 3'-and 5' ends by using the primers denoted as below, and two analysis results were compared to confirm the sequence (Sequence number 4). The protein sequence was deduced from the base sequence (Sequence numbers 5 and 6).

The obtained gene has an open reading frame of 1737 nucleotides corresponding to 579 amino acids. It has been confirmed that there exist N-terminal amino acid sequence and partial amino acid sequences determined in Example 1.

Complimentary primer sequence for 5'-terminal
T G T C G A T G A G G C C C A G T A T 377
826 A G C T C C A G C C A G A T T C C T G 835
1278 C G G T G G A G T G C A C A A C A G A T 1304
1630 C T A C T C T T C C A G C C T A C C C 1648
Complimentary primer sequence for 3'-terminal
1500 C T G G A C T C C T C T C A A C T G T 1482
1152 A A C G G T C T G T G G T A C A C C G 1134
766 G A G A G G T A C C G G T A A G A A G 757
299 T T C G A C C T C C A C T C T T C G C 280

EXAMPLE 5

Isolation of cDNA Encoding 48 kDa Protein

By immunoscreening, cDNA encoding the 86 kDa protein identified in Example 1 was isolated.

To the precipitate obtained by culturing host cells, XL-1-Blue in a shaking incubator in 5 ml of LB medium supplemented with 50 μl of 20% maltose and 50 μl of 1M-MgSO$_4$, 10 mM-MgSO$_4$ was added to have an OD$_{600}$ value of 0.5.

According to a method in the literature (Moon et. al. (1994) J. Biochem. (Tokyo) 116, 53–58), cDNA library of larva of *Tenebrio molitor* was made. To the cDNA library solution, 200 μl of XL-1-Blue was added and cultured in a shaking incubator for 15 minutes at 37° C. The product was mixed with 3.5 ml of top agar preheated to 48° C., and the mixture was poured in a NZY plate. After 4 hours culture at 42° C., a filter treated with IPTG was carefully placed on the plate, and cultured further for 8 hours at 37 ° C. After termination of the reaction, the plate was incubated for 20 minutes at 4° C., and the filter was dried completely in air. Dried filter was washed for 10 minutes at room temperature with high-TBST buffer, and then washed twice with low-TBST solution for 10 minutes at room temperature. The washed filter was dried completely and placed in 3% gelatin solution for blocking at 27° C. for 30 minutes. After drying the filter, it was reacted with antibody solution related to encapsulation protein for 2.5 hours at 27 ° C. After the reaction, the filter was washed three times with low-TBST buffer and reacted in a secondary antibody solution for 30 minutes at 37° C. The filter was washed three times with low-TBST solution and underwent colorization reaction.

The filter prepared as above was colorized by placing in a colorizing agent consisting of 100 ml of AP buffer supplemented with 1320 µl of 50 mg/ml NBT (nitroblue tetrazolium chloride, Bio-rad 170-6532) and 660 µl of 50 mg/ml BCIP(5-bromo-4-chloro3-indoylphosphate -p-toluidine salt Bio-rad 170-6539). The filter was completely dried in air. The purple clones distinguished clearly from surroundings were identified as primary positive clones. Primarily selected positive clones were diluted with SM buffer. That was mixed with 200 µl of XL-1 -Blue expecting to produce 100–200 plaques and then cultured in a shaking incubator for 15 minutes at 37° C. To this 3 ml of preheated top agar was added and poured in a NZY plate. Further procedure to select secondary positive clones was identical to that for primary selection.

To a 50 ml Falcon tube, 200 µl of XL-1-Blue ($OD_{600}$=1.0), 200 µl of positive plaque solution identified through secondary selection ($2 \times 10^5$ phage) and 1 µl of ExAssist helper phage were added and cultured in a shaking incubator for 15 minutes at 37° C. After culture, 3 ml of LB liquid medium was added and cultured in a shaking incubator for 3 hours at 37° C. and then thermally treated for 20 minutes at 70° C. The thermally treated solution was centrifuged for 15 minutes at 1000×g, and the supernatant was stored at 4° C. in a 15 ml falcon tube.

To 200 µl of SOLR cells ($OD_{600}$=1.0), 2 µl and 10 µl of phagemid diluted 10 times with LB liquid medium were added and cultured in a shaking incubator for 15 minutes at 37° C. After culture, 50 µl each was smeareded on LB/ampicillin plate. Since XL-1-Blue pBluescript has an ampicillin resistant gene and the host SOLR cell does not have ampicillin resistance, only transformed SOLR cells with phagemid can grow in a medium containing ampicillin. After incubation for 12 hours at 37° C., single colonies, which were grown on LB/amphicillin plate were cultured for 12 hours at 37° C. in 5 ml LB liquid medium containing 10 µl of ampicillin (50 mg/ml). A DNA purification kit (Promega, wizard plus sv minipreps) was used to isolate and to purify a plasmid inserted with 48 kDa gene from culture broth.

Gene encoding the 48 kDa protein was analyzed by using a commercially available DNA sequencing kit (Perkin Elmer, same as before). Common primers (SK primer and T7 primer) and primers used in sequencing genes for the 56 kDa protein was used to analyze the sequence independently, and two analysis results were compared to confirm the sequence (Sequence number 4). The protein sequence was deduced from the base sequence (Sequence numbers 5 and 6). Ten amino acid residues at N-terminal of 48 kDa protein are identical to 10 amino acid residues of 56 kDa protein from Gly102. Partial amino acid sequences of 48 kDa protein in Example 1 correspond to Gln298-Gly312, Leu363-Gly374 and Thr521-Gln530, respectively.

It was confirmed that this gene is different from any known genes by performing homology search using protein sequence database of National Center for Biotechnology Information (NCBI).

INDUSTRIAL APPLICABILITY

Protein and its gene according to the present invention are physiologically active protein related to inherent immune reaction and can be used as immunostimulants to induce activation of acquired immune reaction. Further, protein and its gene according to the present invention can be used to eliminate disease-mediating parasites such as malaria larva.

What is claimed is:

1. An isolated DNA molecule having a DNA sequence represented by nucleotides 9-2270 of SEQ ID NO. 1, its derivatives or its variants.

2. An isolated protein containing an amino acid sequence represented by SEQ ID NO. 3 or its variants.

3. An isolated protein containing an amino acid sequence represented by residues 18-754 of SEQ ID NO. 3 or its variants.

4. An isolated DNA sequence encoding for a protein containing an amino acid sequence represented by residues 58-1749 of SEQ ID NO. 3 or its variants.

5. An isolated gene containing a DNA sequence represented by nucleotides 58-1749 of SEQ ID NO. 4, its derivatives or its variants.

6. An isolated protein containing an amino acid sequence represented by SEQ ID NO. 6 or its variants.

7. An isolated protein containing an amino acid sequence represented by residues 16-579 of SEQ ID NO. 6 or its variants.

8. An isolated protein containing an amino acid sequence represented by residues 102-579 of SEQ ID NO. 6 or its variants.

9. An isolated DNA sequence encoding for an amino acid sequence of SEQ ID NO. 6 or its variants.

10. An isolated DNA sequence encoding for a protein containing an amino acid sequence represented by residues 16-579 of SEQ ID NO. 6 or its variants.

11. An isolated DNA sequence encoding for a protein containing an amino acid sequence represented by residues 102-579 of SEQ ID NO. 6 or its variants.

12. An immunostimulant composition including an isolated protein containing an amino acid sequence represented by residues 18-754 of SEQ ID NO. 3, an isolated protein containing an amino acid sequence represented by residues 16-579 of SEQ ID NO. 6, and an isolated protein containing an amino acid sequence represented by residues 102-579 of SEQ ID NO. 6 or their variants.

13. A pharmaceutical composition for treating malaria comprising an isolated protein containing an amino acid sequence represented by residues 18-754 of SEQ ID NO. 3, an isolated protein containing amino acid sequence represented by residues 16-579 of SEQ ID NO. 6, and an isolated protein containing an amino acid sequence represented by residues 102-579 of SEQ ID NO. 6 or their variants.

* * * * *